(12) United States Patent
Fox et al.

(10) Patent No.: US 7,025,976 B2
(45) Date of Patent: Apr. 11, 2006

(54) MICRODERMABRASION

(76) Inventors: Richard A Fox, 2903 Humboldt St., Los Angeles, CA (US) 90031; Jerry Whittemore, 3300 Shelby St., Los Angeles, CA (US) 90034

( * ) Notice: Subject to any disclaimer, the term of this patent is extended or adjusted under 35 U.S.C. 154(b) by 0 days.

(21) Appl. No.: 09/972,713

(22) Filed: Oct. 5, 2001

(65) Prior Publication Data

US 2002/0090385 A1 Jul. 11, 2002

Related U.S. Application Data

(60) Provisional application No. 60/239,059, filed on Oct. 5, 2000.

(51) Int. Cl.
*A61K 7/035* (2006.01)
*A61K 7/00* (2006.01)

(52) U.S. Cl. .................. 424/401; 424/69; 424/70.1
(58) Field of Classification Search ............... 424/401, 424/455, 73.02, 69, 70.1
See application file for complete search history.

(56) References Cited

U.S. PATENT DOCUMENTS 4,440,745 A * 4/1984 Schmidt et al. ............... 424/78
5,560,917 A * 10/1996 Cohen et al. ............... 424/401
5,800,816 A * 9/1998 Brieva et al. ................. 424/63

* cited by examiner

*Primary Examiner*—Thurman K. Page
*Assistant Examiner*—Micah-Paul Young
(74) *Attorney, Agent, or Firm*—Wilson Sonsini Goodrich & Rosati

(57) ABSTRACT

The present invention relates to compositions and methods for removing an epidermal portion of the skin of a patient by microdermabrasion with a crystalline emulsion. The crystalline emulsion includes a mixture of coated crystals and a carrier. The coated crystals are formed by combining magnesium oxide, aluminum oxide or a combination of the two with methicone, adding a catalyst, such as ammonia, and mixing, then baking the resulting slurry mixture until the mixture is dry. The coated crystals are able to stay in the emulsion in a carrier.

5 Claims, No Drawings

MICRODERMABRASION

This application claims the benefit of Provisional Application No. 60/239,059, filed Oct. 5, 2000.

FIELD OF THE INVENTION

This invention relates to material for use in microdermabrasion. More particularly, this invention relates to a crystalline emulsion for use in microdermabrasion.

BACKGROUND

Skin rejuvenation is a very active field, both from a dermatologic and an aesthetic angle. Many procedures, including chemical peels, laser treatments and dermabrasion, have been used to treat acne scars, light wrinkles, long sun exposure wrinkles, disfiguring scars, stretch marks, hyperpigmentation, and burns. These procedures are expensive, require a certain amount of recovery time and carry a great risk of side effects and unexpected results. Further, some of these procedures are physician based treatments that require surgical procedure and anesthesia. Thus, these procedures are not accessible to a large segment of the population.

Microdermabrasion was developed a few years ago and is widely accepted due to the absence of complications and shorter recovery time. However, traditional suction microdermabrasion is an expensive procedure which requires large equipment. Further, this procedure is mainly used in salons and spas. As a result, despite the advantages of this procedure over chemical peels, laser treatments and dermabrasion, the number of consumers who have access to this treatment is limited.

Accordingly, there is a need for providing an improved method for skin rejuvenation treatment that is portable, inexpensive, safe, effective and easy to administer.

SUMMARY OF THE INVENTION

The present invention relates to a crystalline emulsion for use in microdermabrasion. The use of this crystalline emulsion in microdermabrasion addresses a number of critical issues: (1) the need to increase access to skin rejuvenation treatment by providing (i) an inexpensive, and (ii) portable, i.e. for use at home, procedure, (2) the need to decrease side effects and recovery times while maintaining effectiveness and increasing safety and (3) the need to create a procedure with easy administration.

The crystalline emulsion provides skin rejuvenation treatment for acne, acne scarring, sun damaged skin, age spots, freckles, stretch marks, fine lines, large pores, scars, keloids and flaking skin. In addition, this invention improves skin texture and enhances and maintains the skin's appearance.

This invention uses the principles applicable in traditional microdermabrasion to provide a skin rejuvenation treatment for use at home with results at least as good as those obtained through use of the machines at salons and spas, while retaining the advantages of decreased side effects and recovery times. The treatment provided for with this invention leaves skin slightly flushed for a few hours, rather than requiring weeks for the skin to heal. Further, this invention is relatively inexpensive compared to traditional dermabrasion with the large machines, laser surgery and chemical peels.

The present invention provides for a crystalline emulsion comprised of a combination of coated crystals and a carrier, where a true covalent bond is formed between the crystals and the coating. The emulsion has a gel-like quality which keeps the emulsion on the skin allowing for easy self-administration. This invention also allows treatment to take place at home without the need for anesthesia, rather than at a physician's office or at a spa or salon.

DETAILED DESCRIPTION OF THE INVENTION

A. Preparation of a Crystalline Emulsion

This invention involves the formation of a true covalent bond between molecules of methicone and the oxide linkages of crystals. The actual polymerization is driven by a three way combination of mechanical energy (mixing rapidly), thermal energy (baking), and a catalyst. The process of preparing crystalline emulsions for application to the skin involves the following steps.

1. Crystals

The crystals of this invention are small and have sharp edges so as to be able to abrade a surface such as skin. The crystals include, but are not limited to magnesium oxide crystals, aluminum oxide crystals or a combination thereof. Preferably, magnesium oxide crystals are used. Materials, such as silicon dioxide, which are rounded function poorly in this invention as they have no edges to abrade a surface.

The crystals used herein are of a particle size about 40–2000 microns, preferably about 100–1200 microns, most preferably about 600–800 microns.

2. Preparation of Emulsion a. Composition

A combination of methicone, crystals and catalyst is used in the invention. The methicone to crystal weight/weight percentage is about 0.01–10.0%, preferably about 0.2–5%, and most preferably about 1–2%. The catalyst is a compound that can be safely used in the production of cosmetics. For example, ammonia and live steam are safe catalysts because they completely vaporize out of the mixture during processing. Ammonia is the preferred catalyst of the invention. The catalyst to crystal-methicone mixture weight/weight percentage is about 0.001–10.0%, preferably about 0.05–4.0%, and most preferably about 1–2%.

b. Mixing

The methicone is cured to the crystals with mixing and the action of a catalyst. The crystals are first mixed with methicone and catalyst. This mixing is preferably performed rapidly. During the mixing covalent bonds are formed between the methicone molecules and the oxide linkages of the crystals. The mixing can be accomplished with a hammermill with a large screen, such as a ¼" screen, or other rapid mixers known to those in the art, such that there is a complete uniformity of coating with the methicone and catalyst on the crystals. The components are mixed until a slurry is formed.

c. Drying

The mixing and formation of a slurry is followed by baking the slurry until the mixture is dry in order to remove the catalyst from the mixture. The baking takes place at a temperature within the range of about 150° F.–450° F., preferably between about 225° F. and about 375° F., most preferably at about 300° F.

Baking is performed until the mixture is dry and the catalyst is removed. Baking occurs for approximately 1 hour when baking at 300° F. The mixture is dry when the water content of the mixture is less than or equal to about 2%, preferably less than about 1%, most preferably less than about 0.1%. The dried mixture of coated crystals is lipophilic and hydrophobic which allows the coated crystals to remain suspended in an emulsion.

d. Testing

The coated crystals can be tested to determine whether true covalent bonds were formed between the methicone and the crystals. First, the coated crystals are placed into a standardized aqueous lotion and allowed to sit for about 12–18 hours. If the methicone is not completely bonded to the crystals, then bubbles of $H_2$ will appear.

e. Emulsion

The final step, after making the coated crystals, is mixing the coated crystals with the carrier to create the crystalline emulsion. The carrier is any gel, lotion, thick solution, cream, paste, wax, or like substance, or any combination thereof known by those in the art that would allow the carrier to hold the coated crystals. The coated crystal to carrier ratio is within the range of about 2%–99%, preferably about 50% (1:2). However, the range may vary with the carrier used, as long as an emulsion can be maintained and sufficient amounts of crystals are present to act as abraders.

Additional compounds may be added to the crystalline emulsion, including, vitamin C, vitamin E, herbal extracts, perfumes, thickeners, surfactants, moisturizers and any other similar compound or combination thereof known to those in the art and desired to be used in a cosmetic.

B. Application of the Crystalline Emulsion to the Skin

A generous amount of the crystalline emulsion should be applied to the skin, for example on the face of a user, avoiding the eye area. The user then gently rubs the emulsion with his/her fingertips, applying light to medium pressure, in a circular motion between about 10 to about 15 times. The rubbing should not exceed about 30 circles in order to prevent excess abrasion of the skin. Then the face is rinsed thoroughly with warm water and patted dry. This procedure can be performed several times a week, preferably about once every 3 to 5 days.

In order to obtain the maximum benefits of the skin rejuvenation treatment, a further embodiment of this invention involves the use of the crystalline emulsion in a system of products that provide complete treatment and skin care. This system involves six phases, the application of the crystalline emulsion being one of these phases.

Phase one involves the use of a face and body cleanser daily. The user should wet his/her face with warm water, work a small amount of the cleanser into a lather, and smooth over the face and body. The cleanser is then rinsed off and the face is patted dry.

Phase two is the application of the crystalline emulsion which should be preferably be done about once every 3 to 5 days.

Phase three involves the daily use of a toner that acts as an exfoliant to remove excess dead skin cells, oil residue and/or dirt and to calm skin redness, minimize pores and condition the skin. The toner is applied to a cotton pad which is gently used to wipe the face. The user should wait about 5 minutes before proceeding to the next phase.

Phase four involves the daily use of a vitamin C collagen gel to protect and nurture new skin cells. A small amount should be applied to the face in a circular motion.

Phase five involves the use of a vitamin enriched sun protecting day moisturizing cream to protect the new skin cells from sun damage, pollution and dehydration. A small amount should be applied to the face twice daily.

Phase six involves the use of an anti-aging treatment cream to increase moisture retention, reduce redness and diminish fine lines. A small amount should be applied to the face at night in a circular motion.

Thus, novel compositions and methods have been described. Various changes may of course be made, without departing from the spirit and scope of the invention.

EXAMPLE 1

Preparation of the Crystalline Emulsion

Magnesium oxide crystals between 600–800 microns in size were combined with methicone, where the methicone to crystal weight/weight percentage was 1–2%. Ammonia was added to the mixture as a catalyst, where the ammonia to crystal-methicone mixture weight/weight percentage was 1–2%.

These three components were rapidly mixed in a hammermill with a large ¼" screen until a slurry was formed and the crystals were uniformly coated with the methicone and catalyst.

The slurry was baked at 300° F. for one hour. After baking, the dried mixture of coated crystals had a water content less than 0.1%.

The coated crystals were tested to determine whether true covalent bonds formed between the methicone and crystals by placing the crystals in a standardized aqueous lotion and allowing the lotion to sit for 18 hours. Bubbles did not appear in the lotion.

The coated crystals were mixed with a gel, where the coated crystals to gel ratio was approximately 1:2, to create the crystalline emulsion.

What is claimed is:

1. An emulsion of covalently coated crystals in a carrier useful for dermabrasion comprising:
   (a) sharp-edged covalently coated crystals selected from the group consisting of: magnesium oxide and a mixture of magnesium and aluminum oxide, where said crystals comprise a diameter of 100–1200 microns, wherein said crystals comprise a covalent coating of 1–2% methicone by weight; and
   (b) an emulsion carrier comprising at least one component selected from the group consisting of: a gel, a lotion, a thick solution, a cream, a pasts, and a wax, wherein the weight ratio of crystals to carrier is 2–99%, wherein the emulsion comprises a gel-like quality sufficient to keep the emulsion on human skin during a skin rejuvenation treatment.

2. The emulsion of claim 1, wherein the covalent coating is characterized for covalent binding of the methicone to the magnesium oxide or the mixture of magnesium and aluminum oxide, by the method of:
   suspending the coated crystals in standardized thick lotion for 12 to 18 hours; and observing the suspension for the presence or absence of $H_2$ formation, wherein the absence of $H_2$ formation is indicative of covalent binding of the methicone to the magnesium oxide or the mixture of magnesium and aluminum oxide.

3. A method of producing the emulsion of coated crystals in a carrier useful for microdermabrasion of claim 1, comprising the steps of:
   (a) providing magnesium oxide crystals or a mixture of magnesium oxide crystals and aluminum oxide crystals;
   (b) mixing the crystals with methicone and a catalyst selected from ammonia and steam, to form a slurry, thereby effecting a covalent interaction of the crystals with the methicone to form covalently coated crystals;
   (c) baking the covalently coated crystals at a temperature in the range of 150–450° F. until the covalently coated crystals are dry and the catalyst is removed; and
   (d) mixing the dry covalently coated crystals with an emulsion carrier at a weight ratio of 2–99% crystals to carrier, wherein the emulsion carrier comprises at least one component selected from the group consisting of: a gel, a lotion, a thick solution, a cream, a paste, and a wax.

4. The method of claim 3, wherein the temperature is about 300° F.

5. The method of claim 3 further comprising testing the coated crystals for covalent binding of the methicone to the magnesium oxide crystals or the mixture of magnesium oxide crystals and aluminum oxide crystals before mixing the coated crystals with the emulsion carrier, said testing comprising the steps of:

suspending the coated crystals in a standardized thick lotion from 12 to 18 hours; and observing the suspension for the presence of absence of $H_2$ formation, wherein the absence of $H_2$ formation is indicative of covalent binding of the methicone to the magnesium oxide or mixture of magnesium and aluminum oxide.

* * * * *